United States Patent
Kowallis et al.

(10) Patent No.: US 6,228,659 B1
(45) Date of Patent: May 8, 2001

(54) METHOD AND APPARATUS FOR MAKING ARRAYS

(75) Inventors: Reid B. Kowallis, Burlingame; Yefim M. Raysberg, Fremont, both of CA (US)

(73) Assignee: PE Corporation ("NY")

( * ) Notice: Subject to any disclaimer, the term of this patent is extended or adjusted under 35 U.S.C. 154(b) by 0 days.

(21) Appl. No.: 09/183,294

(22) Filed: Oct. 30, 1998

Related U.S. Application Data

(62) Division of application No. 60/065,262, filed on Oct. 31, 1997.

(51) Int. Cl.[7] .................................................... G01N 1/10
(52) U.S. Cl. ............................. 436/180; 436/43; 436/47; 436/50; 436/54; 422/63; 422/65; 422/67; 422/100; 422/104; 73/864.22; 73/864.23; 73/864.24; 73/864.25
(58) Field of Search ................................. 436/43, 47, 50, 436/54, 174, 180; 422/63, 65, 67, 100, 104; 73/864.22, 864.23, 864.24, 864.25

(56) References Cited

U.S. PATENT DOCUMENTS

| | | |
|---|---|---|
| 3,164,304 | 1/1965 | Jager et al. . |
| 3,329,964 | 7/1967 | Mutschler et al. . |
| 3,334,354 | 8/1967 | Mutschler . |
| 3,568,735 | 3/1971 | Lancaster . |
| 3,843,053 | 10/1974 | Thoden . |
| 4,023,716 | 5/1977 | Shapiro . |
| 4,165,646 | 8/1979 | Shapiro . |
| 4,351,799 | 9/1982 | Gross et al. . |
| 4,681,742 | 7/1987 | Johnson et al. . |
| 4,699,884 | 10/1987 | Noss et al. . |
| 4,731,335 * | 3/1988 | Brigati ................................. 436/180 |
| 4,952,518 | 8/1990 | Johnson et al. . |
| 5,000,921 * | 3/1991 | Hannaway et al. .................. 422/100 |
| 5,011,779 | 4/1991 | Maimon . |
| 5,046,539 | 9/1991 | MacLeish et al. . |
| 5,226,462 * | 7/1993 | Carl ......................................... 141/1 |
| 5,262,128 * | 11/1993 | Leighton et al. .................... 422/100 |
| 5,338,688 * | 8/1994 | Deeg et al. ........................... 436/180 |
| 5,443,791 | 8/1995 | Cathcart et al. . |
| 5,508,200 | 4/1996 | Tiffany et al. . |
| 5,525,515 | 6/1996 | Blattner . |
| 5,540,889 | 7/1996 | Gordon et al. . |
| 5,551,487 | 9/1996 | Gordon et al. . |
| 5,601,980 | 2/1997 | Gordon et al. . |
| 5,677,195 | 10/1997 | Winkler et al. . |
| 5,736,105 * | 4/1998 | Astle ..................................... 422/100 |
| 5,756,050 | 5/1998 | Ershow et al. . |
| 5,770,151 | 6/1998 | Roach et al. . |
| 5,770,860 | 6/1998 | Franzen . |
| 5,772,966 | 6/1998 | Maracas et al. . |
| 5,807,522 | 9/1998 | Brown et al. . |
| 5,849,598 | 12/1998 | Wilson et al. . |

\* cited by examiner

*Primary Examiner*—Jill Warden
*Assistant Examiner*—Katheryn Bex
(74) *Attorney, Agent, or Firm*—Woodcock Washburn Kurtz Mackiewicz & Norris LLP

(57) ABSTRACT

Apparatus for producing a plurality of arrays of reagent regions is disclosed. A dispensing assembly in the apparatus has a plurality of heads which are spaced for depositing reagents at selected positions in different array areas in a substrate. As the heads in the assembly are advanced along array area, the regions in a row in that array are successively filled, allowing parallel deposition in several array areas at reagent regions which are closely spaced relative to the spacing between deposition heads in the assembly. Also disclosed is a method for producing a plurality of arrays using the apparatus.

12 Claims, 5 Drawing Sheets

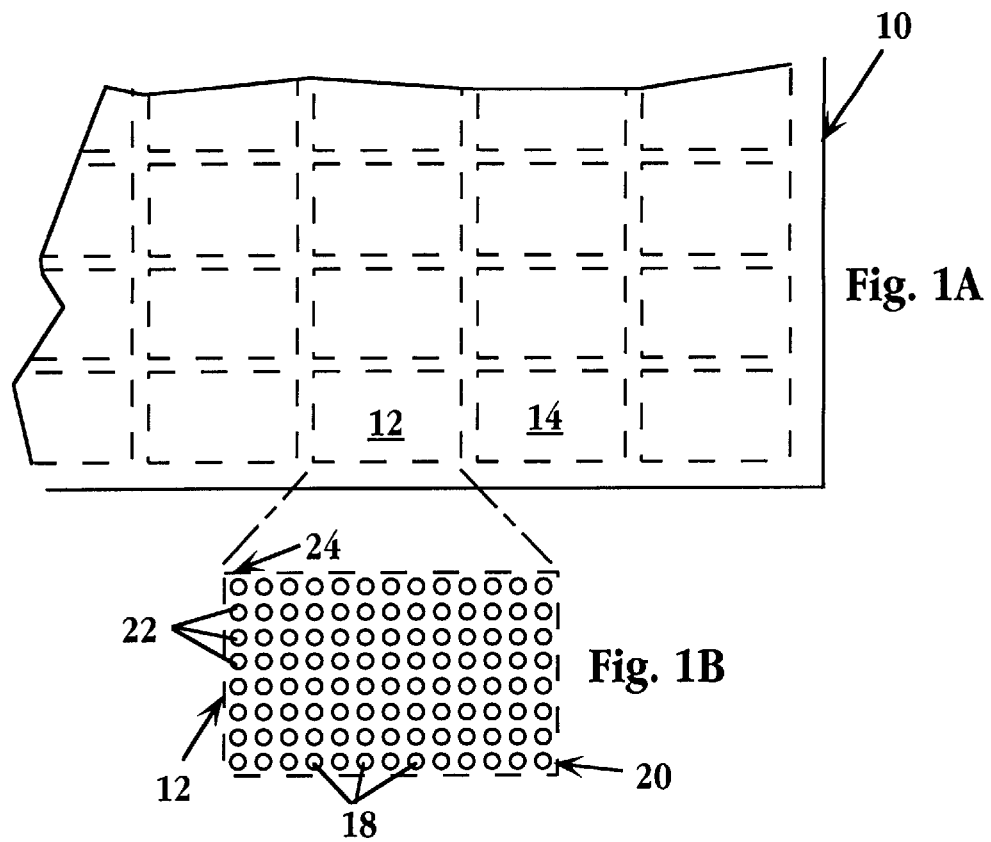
Fig. 1A
Fig. 1B
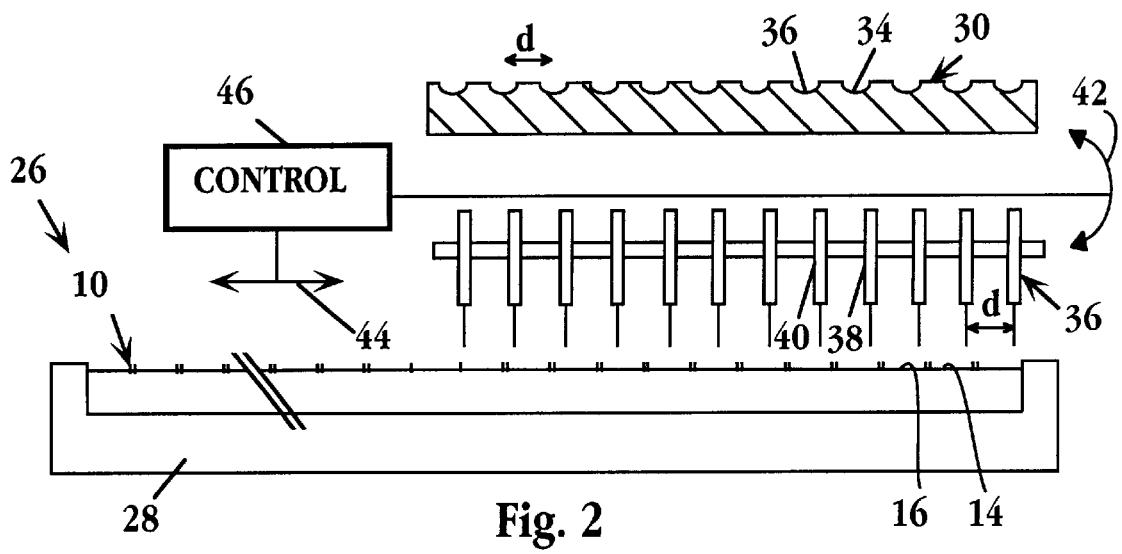
Fig. 2

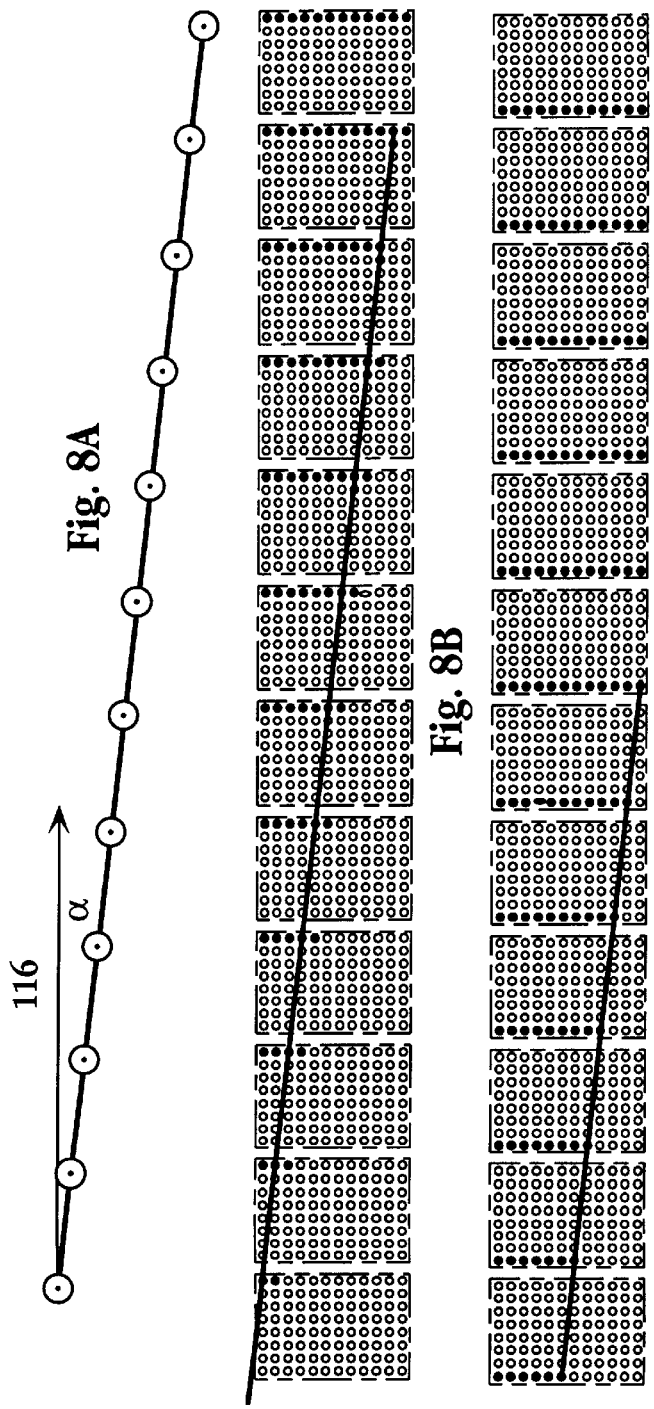
Fig. 8A
Fig. 8B
Fig. 8C
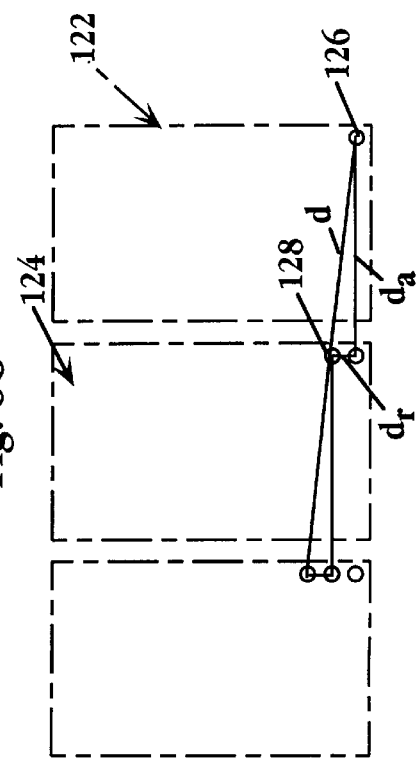
Fig. 9

METHOD AND APPARATUS FOR MAKING ARRAYS

This application claims the priority of U.S. Provisional Application No. 60/065,262 filed Oct. 31, 1997, which is incorporated herein by reference.

FIELD OF THE INVENTION

The present invention relates to microarrays of biopolymers or the like formed on a substrate surface, and to an apparatus and method for producing such microarrays.

BACKGROUND OF THE INVENTION

A variety of methods are currently available for making arrays of biological macromolecules, such as arrays of nucleic acid molecules or proteins. One method for making ordered arrays of DNA on a porous membrane is a "dot blot" approach. In this method, a vacuum manifold transfers a plurality, e.g., 96, aqueous samples of DNA from 3 millimeter diameter wells to a porous membrane. This method is not suitable for making microarrays, i.e., arrays in which the different sample regions in the array are separated by distances of about 1 mm or less.

Microarrays may be made by a robotic arm device that moves successively between a sample-pickup well in a sample array, e.g., a microtitre plate, and a selected microarray position. Although high-density arrays of different biological materials can be constructed by this approach, the production time and efficiency is limited by the fact that the regions of the microarray (or microarrays, if several are being constructed at once) are deposited one-by-one in serial fashion.

Methods for making oligomer arrays on a microchip by parallel step-wise subunit addition have been proposed, e.g., Fodor, et al., *Science* 251:767–773 (1991). This approach uses photomasking to selectively deprotect terminal subunit addition sites in selected regions of the array thus allowing massive parallel subunit addition in building the oligomers on the array. This approach, however, requires relatively expensive processing equipment. It is also not readily adapted to constructing arrays of polymers that are more than about 10–15 subunits in length.

It would therefore be desirable to provide an improved method and apparatus for making arrays, particularly microarrays, employing parallel sample deposition.

SUMMARY OF THE INVENTION

The invention includes, in one aspect, apparatus for producing a plurality of arrays of reagent regions, where each array contains a row of n >1 reagent regions. The apparatus includes a work station for supporting a substrate that can be partitioned into a plurality of array areas, a dispensing assembly having a row of N dispensing heads, each disposed to deposit reagent at a selected one of n different reagent regions in different array area.

In operation, the assembly is advanced successively an incremental distance effective to advance an assembly head from one reagent region in one array area to the corresponding reagent region in an adjacent array area, and to position an adjacent assembly head at a corresponding selected reagent region in an adjacent array area, thus to position each assembly head for deposition at its selected position in an adjacent array area. This operation is effective to position each head successively for deposition at a unique region each array area.

In one general embodiment, the assembly is advanced in the direction of the rows in the array areas, and the head-to-head spacing in the assembly is equal to the sum or difference of (i) the spacing between corresponding reagent regions in immediately adjacent array areas and (ii) the spacing between selected reagent regions in a row in an array area. This embodiment may been carried out with an assembly having a two-dimensional array of dispensing heads, allowing two dimensional microarrays to be formed by parallel deposition.

In another general embodiment of the apparatus, the assembly is advanced in the direction normal to rows in the array areas, with the dispensing heads in the assembly being disposed along an axis that is angular offset from the direction of assembly travel.

The dispensing heads may be pins spaced for simultaneous dipping into the wells of a microtitre plate. Here the structure supplying reagents to the pins includes structure for moving the assembly between positions at which the pins in the assembly are dipped in selected wells in the plate, and positions for reagent deposition on the substrate. In another embodiment, the assembly heads are ink-jet printer heads, and the supply structure includes structure for activating the printer heads.

The invention also includes a method for producing a plurality of arrays of reagent regions, where each array contains a row of n >1, i.e., two or more, reagent regions. The method includes placing in a work station, a substrate that can be partitioned into a plurality of array areas, and advancing over the substrate, a dispensing assembly having a row of N dispensing heads, each disposed to deposit reagent at a selected one of the n different reagent regions in different array areas. The advancing is carried out in incremental distances effective to advance an assembly head from one reagent region in one array area to the corresponding reagent region in an adjacent array area, thus to position each assembly head for deposition at a selected region in an array area. At each new position, the assembly heads are activated for deposition on reagent regions in the array areas. The advancing and head activating steps are repeated until all the regions in a selected row in the array areas have reagents deposited thereon.

In one method, the assembly is advanced in the direction of the rows. In this method, the head-to-head spacing in the assembly is equal to the sum or difference of (i) the spacing between corresponding reagent regions in immediately adjacent array areas and (ii) the spacing between selected regions in a row in an array area. This method may be carried out with an assembly having a two-dimensional array of dispensing heads, allowing two dimensional microarrays to be formed by parallel deposition.

In another embodiment of the method, the assembly is advanced in the direction normal to rows in the array areas, with the adjacent heads in the assembly being disposed along an axis that is angularly offset from the from the direction of assembly travel.

These and other objects and features of the invention will become more fully apparent when the following detailed description of the invention is read in conjunction with the accompanying drawings.

BRIEF DESCRIPTION OF THE DRAWINGS

FIGS. 1A and 1B are plan views of a portion of a substrate showing a plurality of 2-dimensional array areas (1A), and an enlarged view of one array area, showing intended regions of deposition on the array (1B);

FIG. 2 is a partially schematic view of apparatus constructed in accordance with the invention;

FIG. 8A illustrates the angular relationship between direction of assembly movement over a substrate and the axis of the heads on the assembly;

FIGS. 8B and 8C illustrate different stages of deposition on a plurality of array areas, in accordance with the second general embodiment of the invention; and FIG. 9 is an enlarged plan view of the substrate region shown in FIG. 8B, showing the spacing between adjacent dispensing heads in an assembly constructed in accordance with a second general method of the invention.

DETAILED DESCRIPTION OF THE INVENTION

Figure 3:
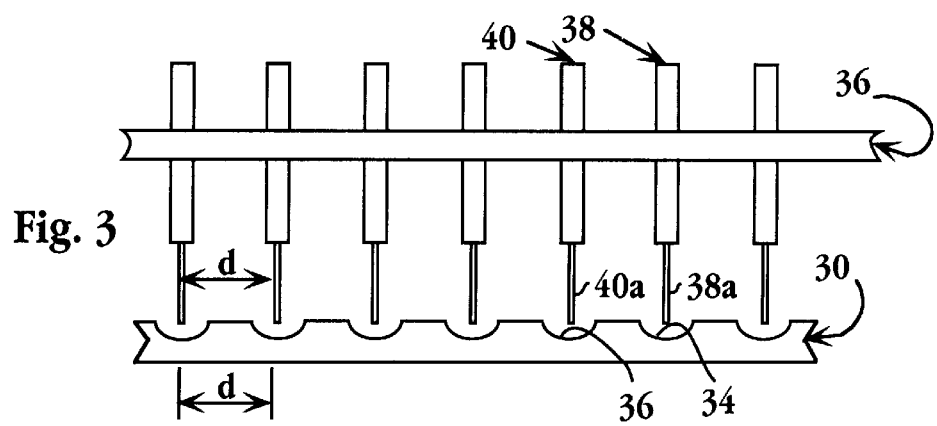
FIG. 3 is a side view of a portion of a head assembly in the invention, shown in registry with the wells in a microtitre plate.

The present invention is designed for producing a plurality of arrays of reagent regions, where each array contains a row of n >1, i.e., two or more, preferably 8 or more, reagent regions having a selected region-to-region spacing. In a typical embodiment, the arrays are two-dimensional arrays of m rows, each with n reagent regions (or n columns, for example), a 8×12 array.

The arrays are formed on a substrate 10 (FIG. 1A) that can be partitioned into a plurality of array areas, such as rectangular areas 12, 14. As an example of a typical array to be formed in each array area, FIG. 1B shows an 12×8 array of reagent regions, such as regions 18 forming a first row 20 in array 12, and regions, such as regions 22 in rows 5–7 of the array. As used herein, the term "row" is generally used to denote the first line of regions formed.

Apparatus for producing the arrays is illustrated schematically at 26 in FIG. 2. The apparatus includes a work station 28 for holding the substrate—in this case, substrate 10. Also shown in FIG. 2 is a microtitre plate 30 containing a plurality of wells, such as wells 34, 36, each designed to contain a reagent that is to be deposited at one region in each array to be formed. Preferably, the plate contains an m×n array of wells corresponding to the M×N regions in each array.

A dispensing assembly 36 in the apparatus includes a row of dispensing heads, such as heads 38, 40, spaced from one another by an effective head-to-head spacing "d" that is substantially greater than the region-to-region spacing in an array row. Typically, the region-to-region spacing in an array is between about 0.1 to 1 mm, whereas the spacing between adjacent heads in the assembly is typically 1 cm or greater. In the embodiment illustrated, the assembly head spacing "d" is equal to the spacing "d" between adjacent wells in plate 30. Although not shown, the assembly is preferably a two-dimensional assembly of heads, with an M×N array of heads corresponding in number and spacing to the m×n array of wells in plate 30.

A robotic arm or track structure, indicated by arrow 42, is designed for moving the assembly between a liquid-uptake position, illustrated in FIG. 3. As shown here, each head, such as heads 38, 40, includes a dispensing pin, such as pin 38a, 40a, respectively, which dips into an associated well, such as well 34, to draw a selected well reagent into the head, e.g., by capillarity.

After fluid pick-up, the assembly is then moved to a position overlying the work station, for dispensing reagents in the assembly heads onto the substrate areas, in a manner to be described below. Structure 42 and plate 30 are also referred to herein, collectively, as means for supplying selected reagents to said dispensing heads, for depositing reagents from the heads onto the array substrate. In the embodiment shown, reagent supply is passive, e.g., by capillary pick-up. It will be appreciated that other supply means are contemplated, for example, where the dispensing heads are ink jet printer heads supply from an on-board reservoir, or through tubing from individual reagent sources.

The apparatus also includes structure, indicated by arrow 44, for moving the assembly successively and incrementally over the work station, to selected deposition positions with respect to the array areas on the substrate. The structure may be a robotic arm or conventional track structure designed to move the assembly by known incremental distance along an X axis (in the direction of the rows in the arrays being formed) or along both X and Y axes (in the direction of both the array rows and columns being formed). The selected movement distances and pattern of movement will be appreciated from the discussion below with respect to FIGS. 4 and 5. Structure 44 is also referred to herein as means for advancing the assembly.

Structures 42 and 44 are each operatively connected to a control unit 46 which controls the operation of the assembly for (i) supply of liquid reagents to the assembly heads, and (ii) deposition of selected reagents at selected array area positions.

Figure 4A:
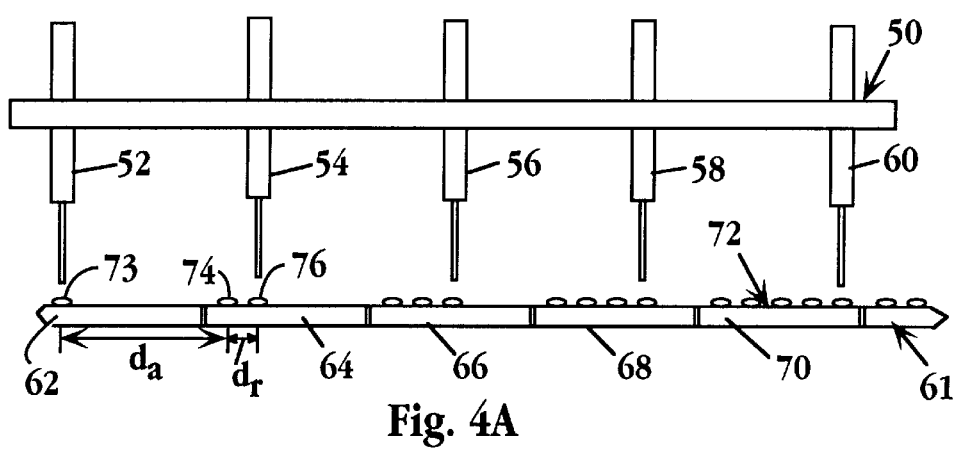
FIGS. 4A–4C illustrate a series of deposition steps on a plurality of array areas, illustrating simultaneous deposition on the arrays in accordance with one general embodiment of the invention.
Figure 4B:
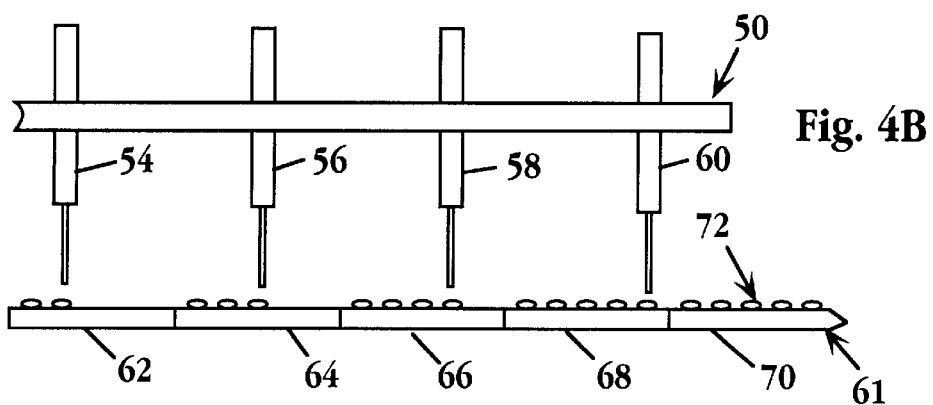
Figure 4C:
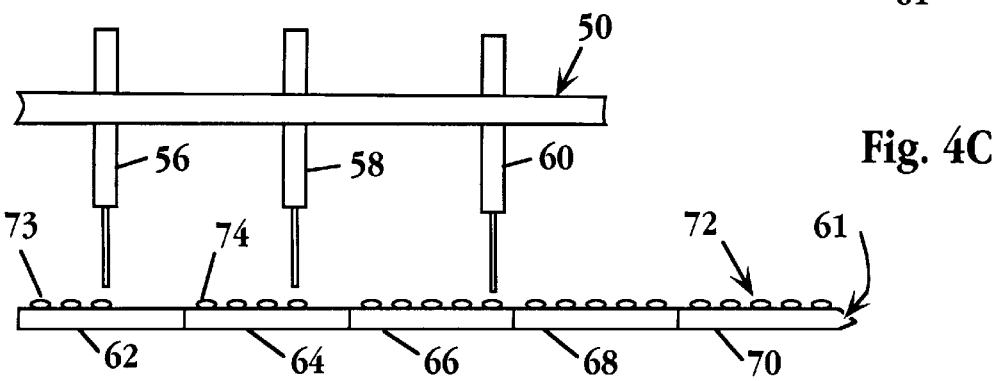

FIGS. 4A–4C illustrate two important features of the invention: (i) the relationship between the spacing between adjacent heads in a dispensing assembly and the spacing between adjacent array areas and adjacent regions in an array on the substrate; and (ii) the successive incremental movements of the assembly in depositing regions on the substrate, in parallel, in several different array areas. The assembly, indicated at 50 in the figures, contains 5 dispensing heads 52, 54, 56, 58, 60, and is designed to deposit in each array area on a substrate 61, such as areas 62, 64, 66, 68, 70, a five-region linear array, such as array 72 in area 70. (The number of assembly heads and array number have been reduced from the 12×8 array described above for purposes of simplifying the description of the assembly operation.)

As seen in FIG. 4A, the distance "d" between the deposition pins in adjacent assembly heads is equal to the sum of the distance "$d_a$" between corresponding first-position regions, such as regions 73, 74 in adjacent array areas, such as areas 62, 64, and "$d_r$", the distance between adjacent regions, such as regions 74, 76 within an array area, such as area 64. Thus, when the assembly is moved to a position to place head 52 for deposition at a first-position region in an area, such as area 62, head 54 is positioned for deposition at the second-position region in the immediately adjacent array area, head 56 is positioned for deposition at the third-position region in the next-immediately adjacent array area, and so forth, such that deposition from each head is occurring in parallel on successive array areas and at successive regions within each area.

After the deposition shown in FIG. 4A, the assembly is now moved (FIG. 4B) to the left a distance "$d_a$" to place head 52 (not shown) at the next left-adjacent area for deposition at the first-position region in that area; head 54, for deposition at the second-position region in area 62; head 58 at the third position region in area 64, and so on. Thus, each head is depositing the same reagent at the same-position region in each array.

This assembly movement, in successive increments of distance "$d_a$", is continued in this fashion, as illustrated in FIG. 4C, until each of the array areas on the substrate has a full five-region array. If the total number of array areas is T, and there are N regions on each array, a total of T×N individual region deposition are made. This requires T+2 (N−1) total incremental movements, where the 2(N−1) term represents the number of assembly movements needed to "walk onto" and "walk off" the substrate area.

In the example illustrated above, the first head is disposed to deposit reagent in the first-position in a row, the second head, at the second position, and so on. In this embodiment, the head-to-head spacing the assembly is equal to the sum of (i) the spacing between corresponding reagent regions in immediately adjacent array areas and (ii) the spacing between adjacent reagent regions in a row in an array area. More generally, the dispensing heads in an assembly are so disposed to deposit a selected reagent at a selected one of the n different reagent regions in different, preferably adjacent array areas. Thus, the only requirement for spacing is that adjacent heads are spaced from one another a distance equal to the sum or the difference of the (i) the spacing between corresponding reagent regions in immediately adjacent array areas and (ii) the spacing between selected reagent regions in a row in an array area.

Figure 5:
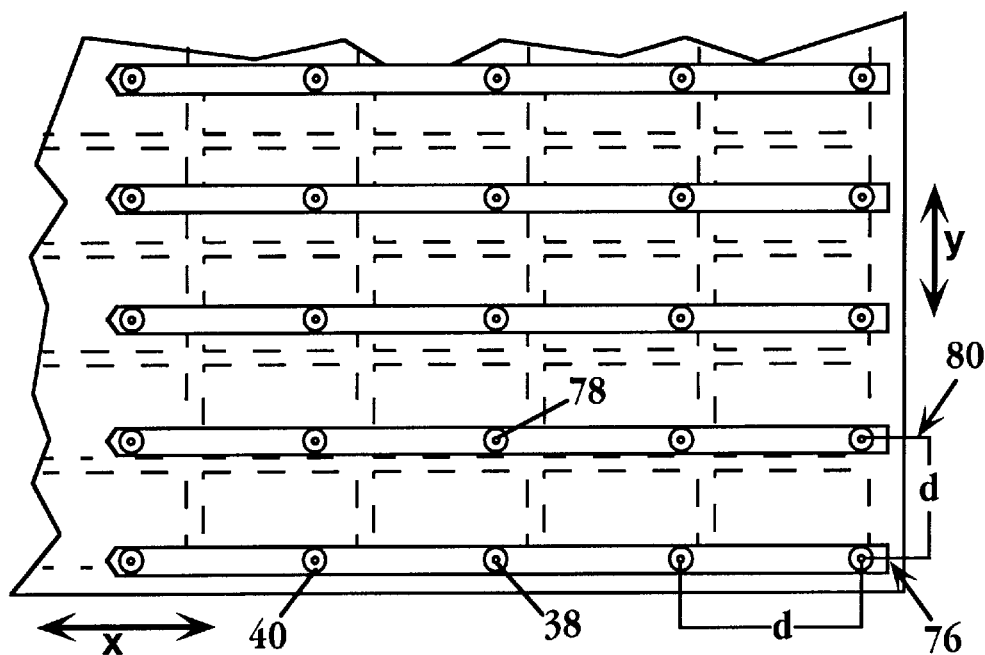
FIG. 5 is a plan view of a portion of a two-dimensional dispensing head assembly placed in deposition position over several array areas on a substrate, in accordance with one general embodiment of the invention.
Figure 6:
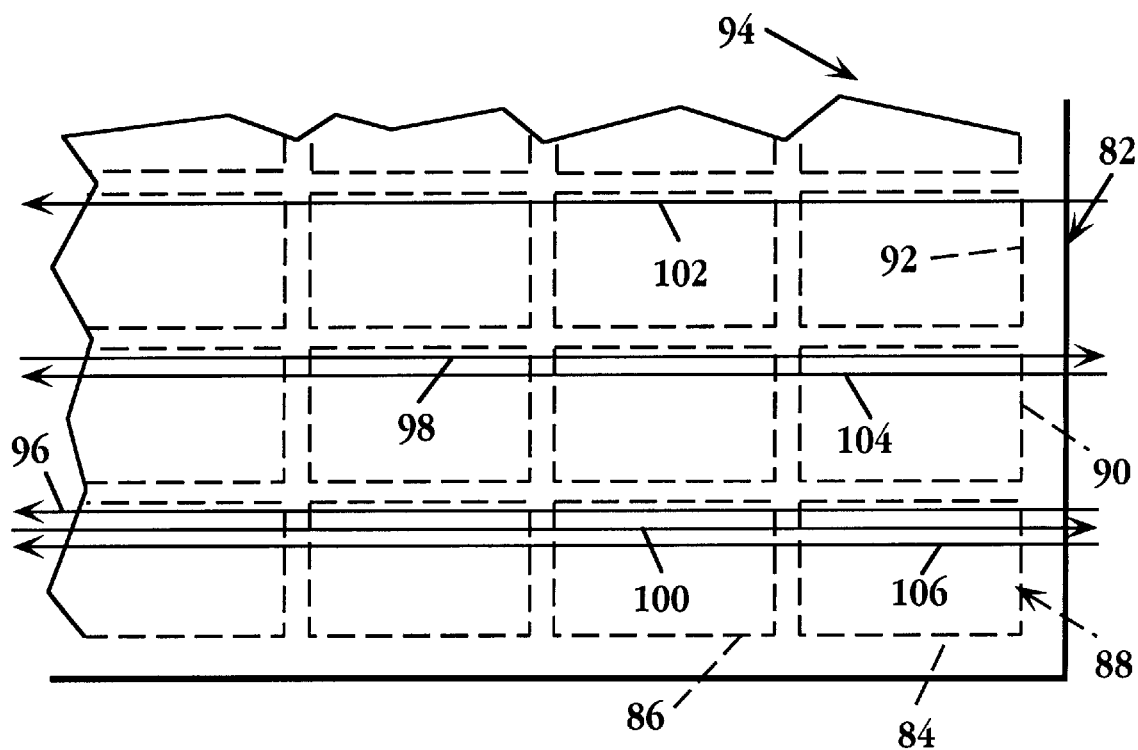
FIG. 6 illustrates initial steps in a deposition pattern used in forming two-dimensional arrays.

With reference again to apparatus 26, FIG. 5 shows the relative spacing of adjacent heads, such as heads 38, 40, in a row 76 in the assembly array, and between adjacent heads in adjacent rows, such as heads, such as 38, 78, in rows 76, 80. In the embodiment shown, the adjacent heads in a row are spaced from one another by a distance equal to the distance between corresponding regions in adjacent array areas along the X (horizontal) axis in the figure, plus the distance between X-axis adjacent regions within an array. Similarly, adjacent heads in a column in the assembly are spaced from one another by a distance equal to the distance between corresponding regions in adjacent array areas along the Y (vertical) axis in the figure, plus the Y-axis distance between adjacent regions within an array. Thus, the heads in row 76 are positioned to deposit reagent in the reagent positions in the first row in each array (the lowermost row in the figure), the heads in row 80, in the second row in each array, and so on. It will be recognized that the spacing between adjacent rows of heads, in the most general case, is such as to place the heads in each row of heads for deposition along a selected row in each array. FIG. 6 illustrates how the just described assembly can be moved to form two-dimensional arrays in two dimensions. The figure shows a substrate 82 having rows of array areas, such as areas 84, 86 in row 88, and columns of array areas, such as areas 84, 90, 92 in column 94.

In the first full translation across the substrate (involving a single row of heads only), the assembly is moved to deposit a row of reagents along the uppermost row of the lowermost array areas, i.e., row 88, in the figure, where the direction of movement and placement of reagent regions is indicated by a solid line 96. The assembly is then moved in the opposite direction, to deposit a row 98 of reagents along the uppermost row of the second from the bottom array areas, i.e., the row containing area 90, and a second row 100 in the next-to-the-top row in the lowermost array areas, by simultaneous deposition from two of the rows of heads. The next full translation of the assembly across the substrate produces the three rows indicated at 102, 104, 106. This process is repeated until each of the array areas on the substrate in the entire m×n array is filled.

Figure 7:
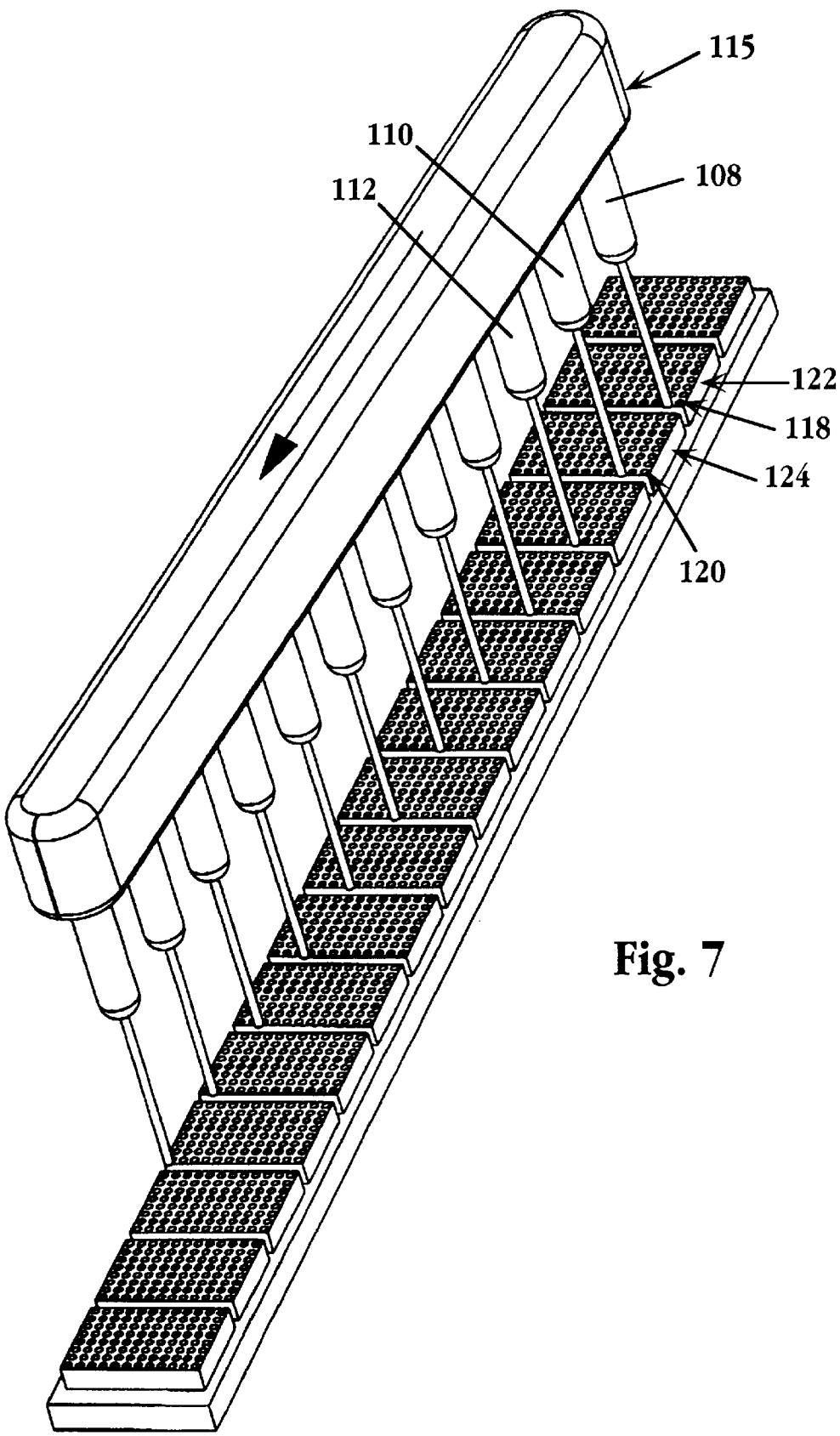
FIG. 7 is a perspective view of a multi-head assembly constructed in accordance with a second general embodiment of the invention, and array areas in a substrate over which the assembly is to be moved.

FIGS. 7–9 illustrate features of an apparatus constructed in accordance with another embodiment of the invention. In this embodiment, the dispensing head assembly, indicated at 115 in FIG. 7, is advanced in a direction normal to the rows of reagent regions which are being created, rather than in the direction of the array rows being created, as in the FIG. 2 embodiment. The direction of travel of the assembly is indicated by line 116 in FIG. 8A; the rows being filled by assembly deposition are the vertically disposed rows, such as rows 118, 120 in array areas 122, 124 in FIGS. 7 and 8B.

As seen in the figures, adjacent heads in the assembly, such as heads 108, 110, are disposed to deposit reagents in reagent regions, such as regions 126, 128 in FIG. 9, that are in adjacent array areas, such as areas 122, 124, and are at corresponding adjacent row positions, e.g., the first row position in area 122 and the second row position in area 124. With continued reference to FIG. 9, the distance "d" between adjacent heads in the assembly is related to the distance "$d_a$" between corresponding regions, such as regions 122, 124 in adjacent array areas, and the distance "$d_r$" between adjacent regions in a row. Specifically, the distance "d" is defined by the right triangle relationship, and is equal to the square root of $d_a^2+d_r^2$. Other features of the apparatus are as described in FIG. 2 for apparatus 26.

In operation, assembly 115 is moved in a left-to-right direction in FIG. 8A, in increments that place the first assembly head at the first-position in a row of each successive array area, the second head at the second position in an adjacent row, and so forth. FIG. 8B illustrates this operation for filling the first column in each array in a bottom-to-top direction in the figure. At the stage shown, the leftmost array row has been completely filled. Six incremental movements later (FIG. 8C), the first six array rows have been filled, and the right six array areas are partially filled with between 6–11 regions, as shown. This operation is continued until all of the first rows in all of the array areas are filled. As in the first embodiment, the number of assembly steps needed to complete the operation is T +2(N−1), where the 2(N−1) term represents the number of assembly movements needed to "walk onto" and "walk off" substrate area.

A second assembly head is used to deposit reagents in the second-row, a third reagent head, for the third row, and so one until each array on the substrate is filled.

Although the invention has been described with respect to specific embodiments and methods, it will be apparent that various changes and modification can be made without departing from the invention.

It is claimed:

1. Apparatus for producing a plurality of arrays of reagent regions, comprising:

a work station for supporting a substrate that is partitionable into a plurality of array areas, wherein each array area contains at least one row, each row formed of n>1 reagent regions;

a dispensing assembly having a row of N dispensing heads, each disposed to deposit reagent at a selected one of n different reagent regions in different array areas;

means for supplying selected reagents to said dispensing heads, for depositing reagents from the dispensing heads onto the array substrate; and means for advancing the dispensing assembly successively an incremental distance effective to advance a dispensing head from one reagent region in one array area to a corresponding n-position reagent region in an adjacent array area, whereby successive advances of the dispensing assembly are effective to position each dispensing head successively for deposition at its selected reagent region in each array area.

2. The apparatus of claim 1, wherein said assembly is advanced in the direction of the rows in the array areas, and the spacing between adjacent heads in the assembly is equal to the sum or difference of (i) the spacing between corresponding reagent regions in immediately adjacent array areas and (ii) the spacing between selected reagent regions in a row in an array area.

3. The apparatus of claim 2, for use in producing a plurality of arrays, each composed of m rows of reagent regions, each row containing n reagent regions, wherein said assembly includes an M×N array of dispensing heads, wherein the N heads in each row in an assembly are each disposed to deposit reagent in a selected one of n different reagent regions in different array areas, and the rows of heads are disposed with respect to one another to deposit reagent at a select one of the m different rows in different array regions.

4. The apparatus of claim 1, wherein said assembly is advanced in the direction normal to rows in the array areas, and the dispensing heads are disposed along an axis that is angularly offset from the direction of assembly travel.

5. The apparatus of claim 1, wherein said dispensing heads are pins spaced for simultaneous dipping into the wells of a microtiter plate, and said supplying means includes means for moving the assembly between positions in which the pins in the assembly are dipped in selected wells in the plate, and positions for reagent deposition on the substrate.

6. The apparatus of claim 1, wherein the dispensing heads of the dispensing assembly are ink-jet printer heads, and said supplying means includes means for activating the printer heads.

7. A method of producing a plurality of arrays of regent regions, comprising:

placing a work station, a substrate that is partitionable into a plurality of array areas, wherein each array area contains at least one row, each row formed of n>1 reagent regions;

advancing over the substrate, a dispensing assembly having a row of N dispensing heads, each disposed to deposit reagent at a selected one of n different reagent regions in different array areas;

activating a dispensing assembly having dispensing heads for deposition on reagent regions in the array areas; and repeating said advancing and activating steps until all the regions in a selected row in the array areas have reagents deposited thereon.

8. The method of claim 7, wherein said advancing is in the direction of the rows in the array areas, and the spacing between adjacent heads in the assembly is equal to the sum or difference of (i) the spacing between corresponding reagent regions in immediately adjacent array areas and (ii) the spacing between selected reagent regions in a row in an array area.

9. The method of claim 8, for use in producing a plurality of arrays, each composed of m rows of reagent regions, each row containing n reagent regions, wherein said assembly includes an M×N array of dispensing heads, where the N heads in each row in an assembly are each disposed to deposit reagent at a selected one of n different reagent regions in different array areas, and the rows of heads are disposed with respect to one another to deposit reagent at a select one of the different rows in m different array regions.

10. The method of claim 7, wherein said assembly is advanced in the direction normal to rows in the array areas, and the dispensing heads are disposed along an axis that is angularly offset from the direction of assembly travel.

11. The method of claim 7, wherein said dispensing heads are pins spaced for simultaneous dipping into the wells of a microtiter plate, and said activating includes moving the assembly between positions in which the pins in the assembly are dipped in selected wells in the plate, and positions for reagent deposition on the substrate.

12. The method of claim 7, wherein the dispensing heads are ink-jet printer heads, and said activating includes activating the printer heads.

* * * * *

UNITED STATES PATENT AND TRADEMARK OFFICE
CERTIFICATE OF CORRECTION

Page 1 of 1

PATENT NO. : 6,228,659 B1
DATED : May 8, 2001
INVENTOR(S) : Reid B. Kowallis, Yefim M. Raysberg It is certified that error appears in the above-identified patent and that said Letters Patent is hereby corrected as shown below:

Title page,
Under U. S. Application Data" please delete "Division of application No. 60/065,262, filed on October 31, 1997" and insert therefor -- claims priority of U.S. Provisional Application Serial No. 60/065,262, filed on Oct., 31, 1997. --

Column 2,
Line 36, please delete the second occurrence of "from the".

Signed and Sealed this

Nineteenth Day of March, 2002

Attest:

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.   : 6,228,659 B1  
DATED        : May 8, 2001  
INVENTOR(S)  : Reid B. Kowallis and Yefim M. Raysberg Page 1 of 2

It is certified that error appears in the above-identified patent and that said Letters Patent is hereby corrected as shown below:

Title page,
References Cited, after U.S. PATENT DOCUMENTS listing, please insert a new sub-heading:

FOREIGN PATENT DOCUMENTS

| | | |
|---|---|---|
| WO 98/28189 | 7/1998 | (WO). |
| WO 97/44134 | 11/1997 | (WO). |
| WO 97/40383 | 10/1997 | (WO). |
| WO 95/35505 | 12/1995 | (WO). |
| WO 89/10192 | 11/1989 | (WO). |
| 196 28 178 | 9/1997 | (DE). |

OTHER PUBLICATIONS

Castellino, A.M., "When the Chips are Down", *Genome Research*, 1997, 7, 943-946.
Editorial, "Getting Hip to the Chip", *Nature Genetics*, 1998, 18(3), 195-197.
Fodor, et al, "Light Directed, Spatially Addressable Parallel Chemical Synthesis", *Science*, 1991, 251, 767-773.
Lemmo, A.V., et al., "Characterization of an Inkjet Chemical Microdispenser for Combinatorial Library Synthesis", *Analytical Chemistry*, 1997, 69(4), 543-551.
International Search Report based on PCT Application No. US98/23092.

UNITED STATES PATENT AND TRADEMARK OFFICE
CERTIFICATE OF CORRECTION

PATENT NO. : 6,228,659 B1
DATED : May 8, 2001
INVENTOR(S) : Reid B. Kowallis and Yefim M. Raysberg It is certified that error appears in the above-identified patent and that said Letters Patent is hereby corrected as shown below:

Column 2,
Line 56, please delete the second occurrence of "from the".

Signed and Sealed this

Sixteenth Day of April, 2002

Attest:

JAMES E. ROGAN
*Director of the United States Patent and Trademark Office*

*Attesting Officer*